United States Patent [19]

Gilding et al.

[11] Patent Number: 4,813,966

[45] Date of Patent: Mar. 21, 1989

[54] BIOCOMPATIBLE MICROPOROUS POLYMERIC MATERIALS AND METHODS OF MAKING SAME

[75] Inventors: D. Keith Gilding, Wheat Ridge; Andrew M. Reed, Arvada; Ian N. Askill, Arvada; Stephen G. Briana, Arvada, all of Colo.

[73] Assignee: Matrix Medica, Inc., Wheat Ridge, Colo.

[21] Appl. No.: 92,643

[22] Filed: Sep. 3, 1987

Related U.S. Application Data

[62] Division of Ser. No. 788,850, Oct. 18, 1985, Pat. No. 4,704,130.

[51] Int. Cl.$^4$ ............................................. A61F 2/06
[52] U.S. Cl. .................................... 623/66; 623/1; 210/490
[58] Field of Search ............... 623/1, 66; 210/488, 210/490; 264/41, 45.5, 45.6, 48; 128/155, 156

[56] References Cited

U.S. PATENT DOCUMENTS 3,978,855 9/1976 McRae et al. ................ 128/156

Primary Examiner—Richard J. Apley
Assistant Examiner—Alan W. Cannon
Attorney, Agent, or Firm—Dressler, Goldsmith, Shore, Sutker & Milnamow, Ltd.

[57] ABSTRACT

A microporous biocompatible material is formed by preparing a segmented polyether urethane urea solution containing 25%±1.5% solids dissolved in a solvent. The solution has sufficient viscosity to be preshaped and formed into the desired thickness of the finished article, then immediately immersed into a precipitation bath in which the solvent in the solution is miscible for a time interval sufficient to cause the solution to set up into an opaque elastomeric article. The article is immediately removed from the bath, any excess solvent extracted and then dried at a temperature on the order of 35° C. to 70° C. followed by heat treating by annealing for approximately sixty minutes at a temperature at 100° C. to 130° C. The void volume of the membrane solution is controlled to within the 50% to 80% range and the pore size from ca<0.1 to several mms. as well as the shape of the pores and solid structures between them, thereby enabling close control over the characteristics and structure of the material as well as over variations in structural characteristics and porosity across the thickness of the material according to its intended application and use.

7 Claims, 2 Drawing Sheets

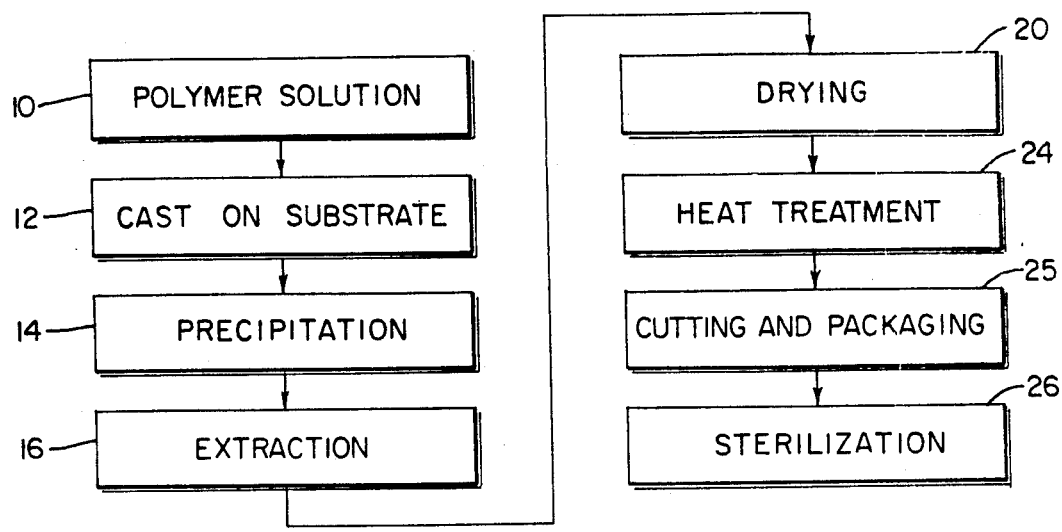
_Fig. 1_
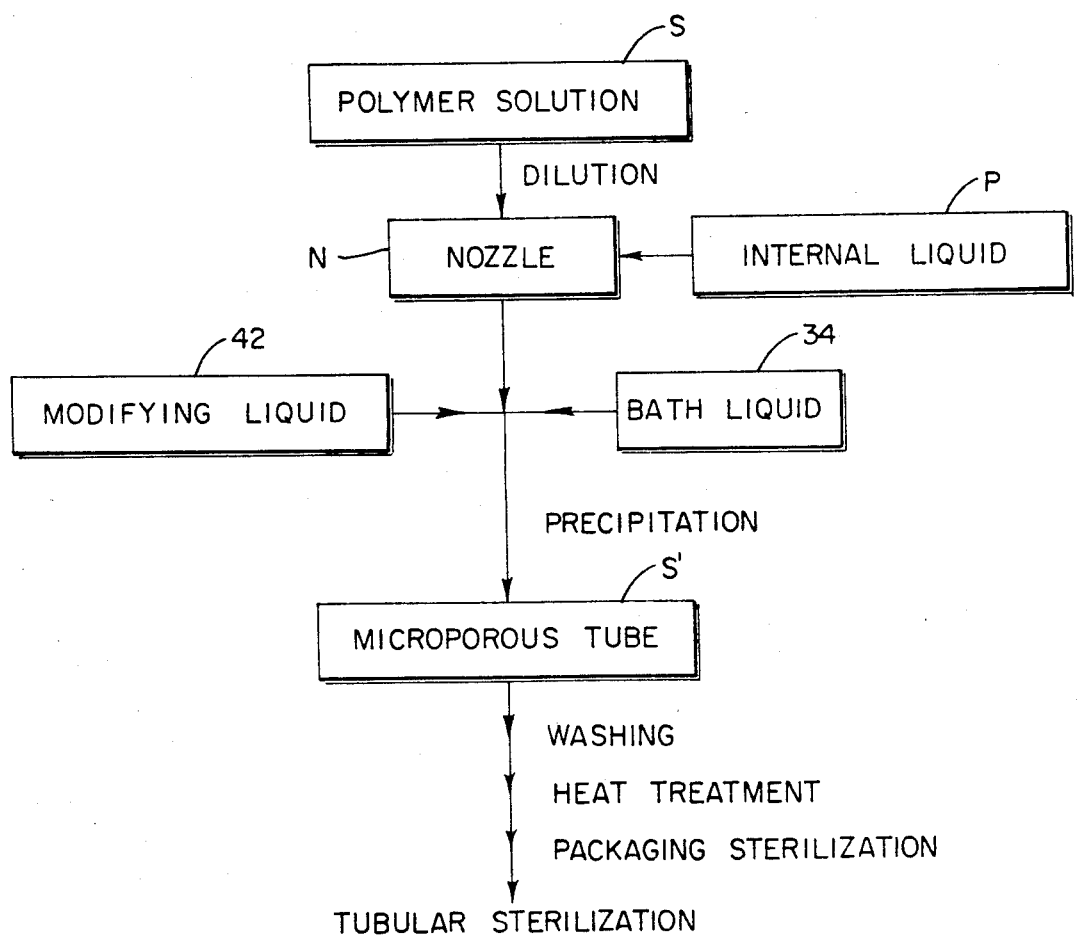
_Fig. 4_

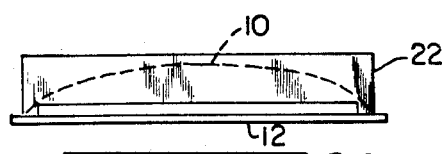
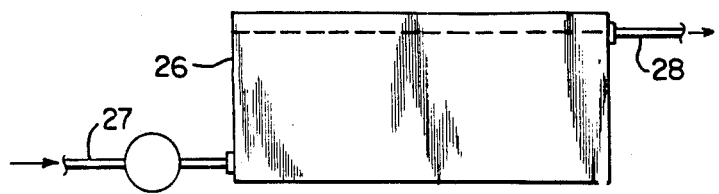
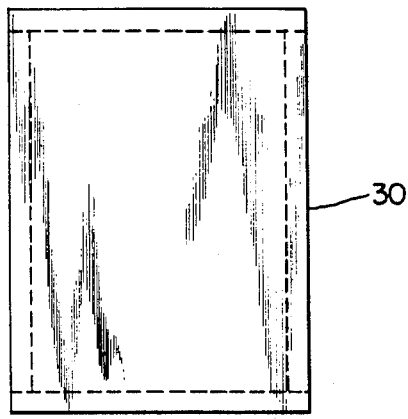
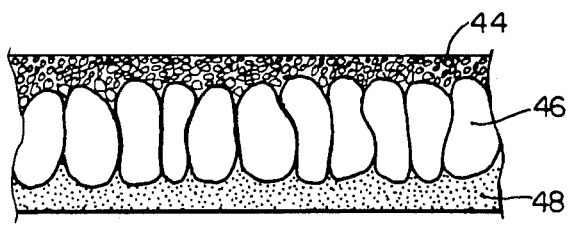
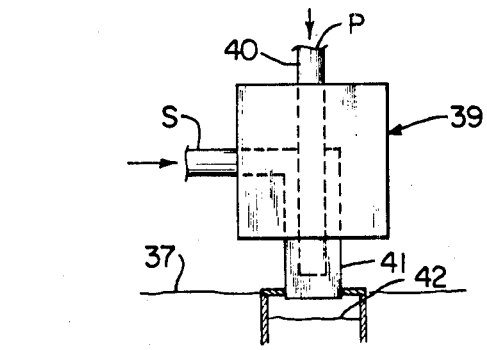
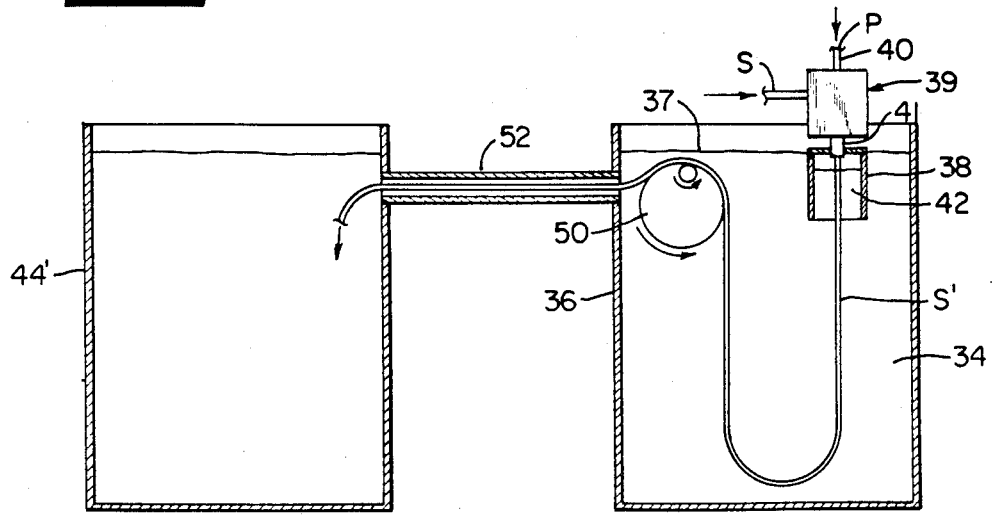

BIOCOMPATIBLE MICROPOROUS POLYMERIC MATERIALS AND METHODS OF MAKING SAME

This is a division, of application Ser. No. 788,850, filed Oct. 18, 1985 now U.S. Pat. No. 4,704,130.

The present invention relates to microporous polymeric materials and to novel and improved methods of forming same for implantation or use in physiological environments.

BACKGROUND AND FIELD OF THE INVENTION

The term "biocompatible" as employed herein means a material that is relatively non-thrombogenic when used in direct contact with blood and is compatible with tissue. Various theories of tissue and blood compatibility of polymeric materials and devices have been advanced over recent years and have resulted in certain controls to the end of making such materials safely implantable into living organisms. Such controls generally can be divided into two categories: (1) materials parameters and (2) structure parameters.

Under the category of materials parameters are hydrophilic/hydrophobic balance, surface energy, chemical nature, and the electrical nature of the surface of materials. Thus, it has been proposed that the higher the water content of the polymer the more closely it will correspond to natural tissue and the greater the level of the biocompatibility. Similarly, it has been proposed that if the surface energy of a synthetic polymer matches that of natural tissue, excellent biocompatibility will result. In the selection of materials, methods have been devised to measure the rate and degree of blood clotting when blood is placed in contact with a synthetic polymeric surface. Also, the presence of an electrical charge is considered to have a substantial effect on its biocompatibility.

The category of structural parameters principally has to do with the mechanical properties, porosity and fiber size of the material. In a vascular prosthesis, compliance is directed to matching the mechanical properties of the host vessel and prosthetic material; whereas, the level of porosity and fiber size selected is concerned more with that which will permit the tissue to ingrow enough to anchor the prosthesis and to promote longterm survival.

A number of problems have been encountered in attaining the desired level of porosity. For instance, arterial prostheses are customarily knits or weaves of DACRON ® or fibrous polytetrafluoroethylene (PTFE). Typically, the porosity of DACRON ® prostheses is on a scale which is visible to the naked eye and results in a preclotting requirement when used surgically for blood conduits. PTFE prostheses are generally made porous by sintering and stretching the PTFE in particle form. Although the porosity of these materials is substantially less than that found in DACRON ® prostheses, it is such that host tissue tends to grow completely through the material and to render it hard, rigid and prone to calcification. Other processes have been devised in an effort to accurately control the porosity of materials. In one process, the voids in a specific type of microporous coral are filled with polymer, and the coral is then dissolved with acid to leave a microporous polymeric structure. In electrostatic spinning processes devised in the past, a polymer in solution is spun into a fiber and laid onto a cylindrical rotating mandrel. The fiber is drawn from the polymer solution by an electric field set up between the mandrel and polymer solution.

Precipitation procedures have been employed in the past, for example, in the formation of thin microporous membranes or filters wherein the pore diameters are of uniform size throughout. Typical procedures for the fabrication of molecular filters are disclosed in U.S. Pat. No. 4,173,689 to Lyman et al, U.S. Pat. No. 3,412,184 to Sharples et al and U.S. Pat. No. 4,203,847 to J. D. Grandine. Thus, U.S. Pat. No. 4,203,847 discloses a process of forming a filter having pores of uniform size and in the range of 250 Angstroms up to 14 micrometers wherein a crystalline polymer solution is applied as a thin film on a traveling belt which is immersed into a precipitation bath that includes a non-solvent for the polymer but which is miscible in the liquid vehicle of the polymer solution. The solution is immersed in the bath until the film has been converted to a porous membrane, after which it is removed from the bath and separated from the belt, any residual solvent being extracted from the membrane and the membrane then dried. Characteristically, the molecular filters in accordance with U.S. Pat. No. 4,203,847 and others are formed out of a crystalline material and are concerned more with the uniformity of pore size in a thin film filter. Similarly, in U.S. Pat. No. 4,173,689, it is said to be necessary to control shrinkage of a membrance by maintaining a uniform pore size throughout. In contrast, applicants' invention is concerned with the biocompatibility of an elastomeric material which is as much as twenty times thicker than filter media and can be reliably and accurately produced by controlled precipitation of a polymer so as to have a selective variation in pore size between its outer and inner skin surfaces with minimal shrinkage. Previous attempts at controlled precipitation of the elastomeric polymers with selective variation in pore size have not been successful, at least in the formation of biocompatible elastomeric materials, principally by reason of the problems associated with controlling the pore size and shrinkage of the material as it is dried.

Polyurethanes and polyurethane ureas in particular are notorious for being difficult to control and reproduce, particularly those utilizing aliphatic diamine chain extenders. In accordance with the present invention, it has been discovered that certain materials selected from the segmented polyetherurethane urea family of polymers, or socalled "spandex" polymers whose chains consist of alternating hard and soft blocks, are suited for use as biocompatible membrane structures when the materials are carefully prepared in solution form with a proper solvent and caused to undergo closely-controlled precipitation, extraction and heat treatment. In particular, it is important that the resultant prostheses have predictably uniform characteristics within close tolerances with respect to tensile strength, elongation and gradation in pore size. The ability to achieve the desired uniformity in characteristics and properties of the prosthesis formed lies in the recognition of those material and structural parameters essential to the formation of a biocompatible structure having the desired characteristics.

SUMMARY OF THE INVENTION

It is therefore an object of the present invention to provide for a novel and improved process for the formation of biocompatible membrane structures and the resultant article of manufacture.

Another object of the present invention is to provide for a novel and improved method for the controlled precipitation of selected polymer solutions in the formation of biocompatible membranes in sheet or tubular form which closely simulate organs in the human body; and further wherein the porosity can be controlled to a level such that the tissue ingrows to a sufficient extent to anchor the material but not enough to prevent its longterm survival.

A further object of the present invention is to provide for a novel and improved process for the controlled precipitation of polyurethane solutions into biocompatible membranes in such a way as to closely regulate the shrinkage and variation in pore size throughout the thickness of the membranes.

It is a still further object of the present invention to provide for a novel and improved process for the preparation of membranes, wound dressings, vascular grafts, ureters and other tubular body vessels from materials having elastomeric characteristics in a closely controlled sequence of steps which permits continuous extrusion of an elastomeric polymer and controlled precipitation, extraction and heat treatment to regulate the porosity, tensile strength and elasticity of the resultant article formed in an efficient and reliable manner.

A microporous biocompatible material is formed in accordance with the present invention by preparing a segmented polyether urethane urea solution containing 25%±1.5% solids dissolved in a solvent and which solution has a viscosity at 22° C.-25° C. between 12,000 and 30,000 cps. The solution has sufficient viscosity that it can be preshaped and formed into the desired thickness of the finished article then immediately immersed into a precipitation bath in which the solvent present in the solution is miscible and for a time interval sufficient to cause the solution to set up into an opaque elastomeric article. The article is immediately removed from the bath and excess solvent extracted, after which the article is dried at a temperature on the order of 35° C. to 70° C. The article is then heat treated by annealing for a time period on the order of sixty minutes at a temperature at 100° C. to 130° C.

An important feature of the present invention resides in the ability to control the void volume of the membrane structure to within the 50% to 80% range, the pore size from ca<0.1 microns to several mms., as well as the shape of the pores and solid structures between them. In particular, the ability to control porosity of the material along its outer or skin surfaces allows the performance of the material to be optimized according to its application. Thus in the case of implant material, it is possible to control interaction of material with particular components of tissue in the body; and, when employed as a surgical or wound dressing, enables close control over the characteristics and structure of the material by selective control of the variation in porosity not only between opposite skin surfaces but of the intermediate bulk or thickness of the material as well. Thus, the present invention resides in a unique method and means not only for controlling the structure and porosity of the material but to impose close controls over variations in structural characteristics and porosity across the thickness of the material according to its intended application and use.

The above and other objects, advantages and features of the present invention will become more readily appreciated and understood from the foregoing detailed description of preferred and alternate embodiments when taken together with the accompanying drawings, in which:

BRIEF DESCRIPTION OF THE DRAWINGS

FIG. 1 is a flow diagram of the preferred process of the present invention employed in the manufacture of membranes;

FIG. 2A is a schematic view of a holding frame for application of the solution to a substrate;

FIG. 2B is a side elevation of a precipitant tank;

FIG. 2C is a top plan view of a holding tray;

FIG. 2D is a top plan view of a drying frame;

FIG. 3 is a cross-sectional view of a membrane formed in accordance with the process described in FIGS. 1 and 2;

FIG. 4 is a flow diagram of a preferred process employed in the manufacture of vascular grafts and other tubular prostheses;

FIG. 5 is an enlarged view of the solution feed block and nozzle employed in forming a vascular graft; and FIG. 6 is a cross-sectional view of one form of precipitant bath and extraction tank employed in the formation of a vascular graft.

DETAILED DESCRIPTION OF THE PREFERRED EMBODIMENT

Referring to the flow diagram of FIG. 1, there is schematically illustrated the process for forming microporous, elastomeric membranes with a maximum pore size on the order of 100 microns and a thickness on the order of 0.025". The segmented polyurethane urea solution represented at 10 is first cast onto a series of substrates in the form of glass plates 12. Each plate should be clean and dry and have a surface area for application of the solution corresponding to that of the size of the finished article. Although glass is the preferred substrate, other materials may be used, such as, TEFLON®, polyethylene or stainless steel. The preferred or optimum range of thickness for the solution is on the order of 0.035" to 0.045".

A precipitant bath as at 14 is provided by filling a tub large enough to accommodate several plates with a precipitant which is miscible with the solvent present in the polyurethane solution but not with the solution itself. The temperature of the precipitant bath is 5° C. to 25° C. The composition of the precipitant may vary depending upon the porous structure desired and, in the case of polyurethane urea solutions containing a solvent in the form of dimethyl acetamide (DMAC) or dimethyl formamide (DMF), the bath composition may be an aqueous solution of alcohols, such as, methanol, ethanol, proponal or isoproponal, or aqueous mixtures of solvents for the polymer being used. In certain cases, non-aqueous solutions may be utilized either alone or in combination at various concentrations which are miscible with the solvent.

In the casting process as shown in FIG. 2A, the polyurethane solution 10 is poured onto a glass plate or substrate 12 and a casting bar 22 is then slowly advanced by sliding across the glass plate 12 so as to uniformly spread the solution across each plate 12. Any excess solution is removed from the casting bar as the solution is applied to each plate. Each plate 12 is immediately immersed into the precipitant tub 14 and left to stand for a period on the order of ten minutes to an hour, or long enough to precipitate the casting solution onto the plates 12 and form a membrane-like layer. The membrane is peeled from each plate while still in the precipitant bath and then removed from the bath and placed into an extraction tank 26 with the shiny side of the membrane facing up.

As shown in FIG. 2B, an extraction tank 26b is filled with filtered water via inlet 27 to a level opposite a drain port 28. A rectangular extraction frame 30 illustrated in FIG. 2C is placed over the membrane and forced underwater to retain the membrane at the bottom of the extraction tank 26. All membranes are similarly peeled off their substrates 12 and placed into the extraction tank as described above so as to be stacked on top of one another and separated by the extraction frames 30. Preferably, the membranes are left in the extraction tank 26 for a minimum period of fifteen hours but no longer than forty hours. In the extraction stage 16, water is constantly run through the extraction tank 26 at the rate of four to eight liters per minute to completely flush or remove any of the solvent and precipitant solution from the membranes.

After the extraction stage, excess moisture is removed from the membrane sheets by removing the extraction frames 30 and membranes from the extraction tank 26 and placing each membrane over a drying frame 32 as shown in FIG. 2D. In the drying stage 20, each membrane is centered on a drying frame 32 and attached to the frame by suitable means, such as, masking tape 33 applied along the edges of the membrane. The drying frames or racks with attached membranes are advanced through a clean room and then placed in an oven when they are dried for a minimum of four hours and a maximum of seven hours at a temperature of 50° C.±5° C., all as represented at 20 in FIG. 1.

Upon drying, the membranes or patches are inspected, cut loose from the drying frame along the edges just inside the masking tape and are individually placed in an autoclave bag. The bags with enclosed membranes are then evenly distributed over a rack in an oven for the purpose of heat treating the membranes. Care should be taken to maintain the autoclave bags and membranes perfectly flat, and the oven temperature is set to 120° C. In the heat treatment or annealing step 24, the membranes are heated for a period of one to one and a half hours at the desired temperature level after which the oven is turned off and the membranes permitted to cool in the oven. The autoclave bags and enclosed membranes are then removed from the oven and placed under a laminar flow hood for further processing and packaging as represented at 25. Upon removal from the heat treating oven, the patches are sterilized as at 26 by irradiation, such as, cobalt 60 gamma irradiation in the range of 0.5–4.0 megarads.

Preferably, the process as hereinbefore described is carried out using one of the segmented polyether urethane urea family of polymers, or "spandex" polymers whose chains consists of alternating hard and soft blocks. The soft blocks have glass transition temperatures ($T_g$s) below the use temperature or 0° C., and the hard blocks have $T_g$s above the use temperature, or 100° C. A preferred substance is that sold under the trademark MITRATHANE TM manufactured and sold by Mitral Medical International, Inc. of Denver, Colo. which is produced as a 25% w/v solution in dimethyl acetamide (DMAC) of 12,000–30,000 centipoise viscosity. In MITRATHANE TM, the hard blocks are extremely short; however, the interchain interaction is enhanced by a hydrogen bonding system which is produced by four hydrogen bonds acting in concert within each hard segment. This molecular structure produces the necessary properties in solution which will result in a variety of microporous structures. For instance, under controlled precipitation as described in relation to FIG. 1, the resultant membrane is a microporous structure having on the order of 50% void volume with a difference in pore size, for instance, of <0.10 microns at the exposed surface to 100 microns at the surface contacting the substrate. The structure and porosity of the MITRATHANE TM microporous structures can be altered by adjusting any or all of the following variables:

(a) Percent polymer in solution—increasing the solids content of the polymer solution will increase the viscosity of the solution and decrease the pore size in the resultant membrane.

(b) Molecular weight of polymer in solution—increasing the molecular weight of the MITRATHANE TM will decrease the pore size of the resultant membrane.

(c) Solvent/non-solvent ratio of the polymer solution—decreasing the solvating power of the solvent or solvent/non-solvent in which the polymer is dissolved will result in a membrane with smaller pores.

(d) Temperature of polymer solution—increasing the temperature of the polymer solution will increase the relative solubility of the polymer and lead to increased membrane porosity.

(e) Type of non-solvent in precipitation bath—choice of non-solvents whose solubility parameters indicate that they are almost solvents for polyurethane will lead to membranes with larger pore sizes. Use of non-solvents whose solubility parameters indicate that they are far from being solvents will lead to membranes with smaller pore sizes.

(f) Solvent/non-solvent ratio in precipitation bath—as in (e) above, solubility parameters of mixture will determine pore size; close to being a solvent, large pores and far from being a solvent, small pores.

(g) Temperature of precipitation bath—the higher the temperature of the precipitation bath the more open the pore structure of the resulting membrane.

(h) Speed of immersion of polymer solution in precipitation bath—the faster the immersion, the tighter the pore structure of the resultant membrane. For instance, when the membrane is to be employed as a cardiac patch, the skins which are visible on each side of the membrane are semi-permeable so as to allow passage of small molecules only, such as, those on the order of 1500 molecular weight but not allow protein transport which would lead to ultimate tissue "grow-through".

In the manufacture of vascular grafts or small bore tubes, a similar sequence of steps is followed to that employed in the preparation of flat membranes described with reference to FIGS. 1 and 2. As shown in FIGS. 5 and 6, a tub or container 36 is substantially filled with a precipitant solution 34 and filled to a level as designated at 37. A nozzle block 39 contains spaced inner and outer concentric tubes 40 and 41 which are suspended above the container 36 for downward vertical extension centrally of the upper end of the container 36 with their lower extremities terminating directly opposite to the upper edge of the container 36, and the inner tube 40 having its lower edge terminating just above that of the outer tube 41. The lower end of the nozzle has an annular flange which supports a retaining tube 38 for downward extension into the solution 34 in the container 36.

The tubular structure of the graft is formed by extruding a polyurethane solution S through the concentric or annular space between the inner and outer tubes 40 and 41 downwardly through the retaining tube 38 and into the precipitant bath 34. Selective control over the porosity of the material is achieved both internally and externally by pumping an internal precipitant solution P through the inner tube 40 at a comparative rate to the polyurethane solution. As the precipitant solution P contacts the solution S beneath the inner tube 40 it will establish a gradient or rate of precipitation to alleviate forces otherwise tending to cause the outer wall to collapse into the inner wall as the solution S begins to precipitate. The resultant tubular prosthesis S' advances into the precipitant bath where it remains immersed in the bath for a period on the order of at least ten minutes and a maximum of sixty minutes. As the polyurethane coagulates into a tubular prosthesis S', it is advanced through the precipitant bath as illustrated then drawn over a rotating drum member 50 through conduit 52 into an extraction tank 44' where it is flushed with an extraction solution, such as, water or an isotonic saline to remove residual solvents or precipitants. The resident time of the prosthesis S' in the precipitant bath 34 is regulated by the speed of rotation of the drum 50 in relation to the pumping rate of the solutions into the nozzle 39. In the extrusion process described with respect to FIGS. 3 to 5, one side of the nozzle is capable of forming different sized tubular prostheses by control of the pumping rate, the size of the microporous tube ranging from 1 to 10 millimeters ID. In the vascular graft manufacture, the variation in pore size between the outer wall and the inner wall corresponds very much to that experienced in the cardiac patch or membrane manufacture. When a saline solution was employed in place of the DMSO/water mix as the capillary solution, the pore size did not change along the inner wall but nevertheless the saline solution was operative to prevent a collapse of the wall and was of sufficient density to cause the tubular prosthesis to descend through the precipitant bath.

Generally, the extraction step as described requires from fifteen to forty hours for complete removal of any excess solvent. Following the extraction step, the prostheses are heat treated, packaged and sterilized for the time periods and temperatures described with respect to the membrane formation of FIG. 1.

The surfaces of the tubular prothesis may be further modified by passing the extruded member through a modifying liquid 42 placed in the retaining tube 38 above the precipitant bath 34 so that the external surface is brought into contact with the modifying liquid preliminary to immersion in the bath to facilitate finer control over the outer surface porosity. In a preferred process for preparation of vascular grafts, a MITRATHANE TM polymer solution was extruded to form an internal diameter in the range of 2 mm to 10 mm and a wall thickness of 0.20 mm to 2 mm. The polyurethane is injected through the nozzle at a flow rate on the order of 0.5 ml/min. to 20 ml/min. and the internal solution P flowing at a rate of 0.5 ml/min. to 50 ml/min. The polymer solution with a DMAC solvent was precipitated in a bath containing 0.9% sodium chloride solution in water at 25° C. with a capillary precipitant of 30% DMSO in water. The DMSO/water solution is of a greater density than the bath solution and will therefore remain trapped in the tubular member and retard the rate of precipitation along the inner wall as well as to encourage it to descend into the bath by gravity. A modifying liquid 42 of DMAC was used between the nozzle and the precipitant bath to retard the rate of precipitation and control the porosity to a degree dependent upon the depth of liquid in the outer tube 38. The foregoing method was used in the preparation of a vascular graft having a porosity which would allow the transport of water, ions and low molecular weight species of less than 2,000, but will not permit ingrowth or adhesions on the external surface or internal, lumenal surface.

It has been found that tubular polyurethane protheses may be prepared as described in the above from most, if not all, segmented polyurethane urea compositions at concentrations varying from 10% to 30% solids and formed with a number of different solvents, such as, DMAC, DMSO, DMF, THF and combinations thereof. The bath and capillary precipitants may consist of any liquid or combination of liquids and dissolved solids that fulfill the criteria of being a non solvent for the chosen polyurethane yet are miscible with the solvent for that polyurethane. Again, the modifying liquid 42 may be a solvent or "near" solvent for the polyurethane solution, such as, dimethyl acetamide which is utilized as described to control pore size; also, it will serve to prevent collapse of the tubular member in advancing downwardly through the bath.

EXAMPLE I

Microporous Membrane Manufacture

A MITRATHANE TM polymer solution was used conforming to the following specifications: 25%±1.5% solids dissolved in dimethyl acetamide (DMAC). Viscosity at 22° C.–25° C. between 12,000 and 30,000 cps. The polymer solution was spread onto a glass plate (approximately 12"×10") to a thickness of between 0.030"–0.045". The glass plate with cast polymer film was quickly immersed in a precipitation bath. The composition of this bath will vary depending upon the type of porous structure required for the end product. Typically, it will contain mixtures of water, alcohols and water/solvent solutions. For the manufacture of the cardiac patch and wound dressings, this bath is water. After ten minutes immersion in the precipitation bath the polymer film had precipitated into an opaque white elastomeric sheet. This sheet was removed from the glass plate and placed in the extraction tank to remove residual solvent. Extraction was accomplished by holding the sheets under running water for a minimum period of fifteen hours. After extraction the sheets were affixed to Plexiglas drying frames and dried in a forced hot air oven at between 35° C. and 70° C. Drying was accomplished in three to six hours. After drying, the films were removed from their respective frames and placed in autoclave bags. The sheets in autoclave bags were then annealed in a forced air oven for one to three hours at 100° C. to 130° C. The processed patches are then cut to size with a steel ruled die and double packaged in polypropylene peel-pouches. The packaged material was then sterilized by gamma irradiation ranging from 0.5–4.0 megarads.

EXAMPLE II

Microporous Vascular Graft Manufacture

A MITRATHANE TM polymer solution conformed to the following specifications: 25%±1.5% by weight solids dissolved in dimethyl acetamide (DMAC). Viscosity measured at 22° C.–25° C. between 12,000 and 50,000 cps. The solution was passed through an extrusion nozzle as shown in FIG. 4. The polymer solution was pumped such that it was extruded in a cylindrical form from the space between the two cylinders. Simultaneously, a non-solvent was extruded through the central orifice and which acts as a non-solvent or precipitant for the polymer. The overall extrudate was allowed to pass through a bath of non-solvent. The effect was to extrude a tube of polymer solution which precipitated both from the inside and the outside simultaneously so that the wall structure had a controlled thickness and microporosity. The physical properties may be altered at will by the size of the respective nozzle and the composition of the capillary solution and precipitation bath. Fine control over the porosity of the outer surface of the graft may be exerted by passing the graft through a "modifying" solution before ultimate precipitation/coagulation in the precipitation bath. Typically, to produce a 5 mm ID artery, the respective nozzle insert is placed in the nozzle block. The polymer flow and capillary flow are set to the desired flow rates (polymer flow 0.5 mls-20.0 mls, capillary flow 0.5 mls-50 mls). Once these values have been obtained and have stabilized, the nozzle is placed directly in contact with the precipitant bath, such as, isotonic saline, or the surface of the modifying solution above the bath such that no air gap exists between the nozzle and the surface of the bath. Microporous arteries will be extruded and precipitated. After a minimum of ten minutes in the precipitant bath, the artery was washed internally and externally with sterile filtered saline for a minimum of forty hours to remove traces of residual solvent. The washed artery was cut to the desired lengths. The artery, immersed in saline, can be heat treated to optimize mechanical properties by autoclaving at 121° C. for sixty minutes. The arteries were then packaged in polycarbonate tubes still in isotonic saline and were then sterilized by gamma irradiation at 0.5-4.0 megarads.

EXAMPLE III

Vascular Graft Formation

The steps outlined in Example II were followed in precipitating a 25% polyether urethane urea in a DMAC solution, using an internal precipitant of 30% DMSO in water and a bath precipitant of 0.9% sodium chloride solution. A modifying solution of acetone was used to form an external surface with two to five micron pores. The resultant prosthesis had a smooth inner surface impermeable to molecules of greater than 2,000 molecular weight and a microporous outer wall which would permit ingrowth sufficient to immobilize the prosthesis in the tissue bed but not permit severe loss of compliance or calcification.

EXAMPLE IV

Vascular Graft Formation

The method of Example II was followed to prepare a tubular elastomeric structure with sufficient lumenal porosity to anchor any lumenal ingrowth that may occur from the anastomoses while allowing the exterior wall to be freely sliding within the tissue bed. The process was modified by preparing the graft by precipitation of a 17.5% solid solution of MITRATHANE ™ in a solvent composed of 62% DMAC and 38% DMSO. The internal precipitant was prepared from 56% DMSO, 24% methanol and 20% water. Again, the precipitant bath was 0.9% sodium chloride solution. The resultant porosity of the internal surface was 3 microns to 10 microns and the external porosity on the order of 20 Angstroms.

EXAMPLE V

Microporous Membrane Formation

A spandex polymer solution sold under the trademark BIOMER ® was diluted with dimethyl acetamide (DMAC) to form a solution containing 15% by weight of solids. This solution was cast onto a glass plate to a wet thickness of 0.024". The temperature of the solution was 21° C.±2° C. The plate plus cast solution was immersed in a water bath maintained at 15° C. The polymer was precipitated out of the solution while in the water bath. The total time elapsed in the water bath was eighteen hours. The membrane thus formed was dried while being constrained at 50° C.±5° C. for two hours. The resulting porous structure was examined by scanning electron microscopy to reveal a structure consisting of a surface layer with pores in the range of 0.1 microns to 1 micron under which lies a substructure with "finger-like" voids of approximately 100 microns×200 microns. The membrane mechanical properties were quantified using an Instron tensile tester. The membrane having an ultimate tensile strength of 0.26 kg/mm² and an elongation at break of 480%.

EXAMPLE VI

Microporous Membrane Formation

Another spandex type polymer sold under the trademark PELLETHANE ® 80AE was dissolved in dimethyl acetamide (DMAC) to give a 20% by weight solution. Dissolution was accomplished by gentle agitation at ambient temperatures for twenty-four hours. The solution was cast onto a glass plate to a wet thickness of 0.024". The temperature of the solution bath was 21° C.±2° C. The plate was immersed in a water bath maintained at 15° C., and the polymer precipitated out of the solution while in the water bath. The total time elapsed in the water was eighteen hours. The membrane sample thus formed was dried while being constrained at 50° C.±5° C. for two hours. The resulting porous structure was examined by scanning electron microscopy. The structure consisted of a surface layer with pores approximately 2 microns to 15 microns and a substructure with "finger-like" pores of approximately 200×500 microns. The membrane's mechanical properties were quantified using an Instron tensile tester, the membrane having an ultimate tensile strength of 0.12 kg/mm² and an elongation at break of 350%.

EXAMPLE VII

Wound Dressing

A wound dressing was prepared according to the steps outlined in Example I but where the polymer solution was spread to a thickness of between 0.005" to 0.045". After immersion in the precipitation bath for ten minutes the sheet was removed and extracted under running water for a period of fifteen hours. Thereafter, the sheets were affixed to drying frames and dried for a period of two to six hours at a temperature ranging from 35° C. to 70° C. The resultant membrane had a porosity of 1 micron to 3 microns on one side and less than 0.2 microns at the opposite side or surface, the opposing surfaces being separated by an intermediate layer composed of relatively large intersticial voids.

EXAMPLE VIII

Wound Dressing Manufacture

To increase the potential exudate handling capacity of the wound dressing, the pore size along the surface to be placed in contact with the skin was increased by using methanol in the precipitation bath and increasing the immersion time in the bath to 20 minutes. The resultant wound dressing had a porosity of 3 microns to 7 microns on the skin contacting surface and a porosity of less than 0.2 microns on the opposite or external surface.

EXAMPLE IX

Wound Dressing Manufacture

In order to further increase the pore size, potential exudate handling capacity and moisture vapor transport, the concentration of the polymer in solution was reduced from that described in Examples VII and VIII. Thus, a polymer solution was used having 10%±1.5% solids dissolved in DMAC with a viscosity of 23° C. to 25° C. between 1,000 and 15,000 cps. The solution was spread to a thickness of between 0.030" and 0.045" and immersed for a period of 20 minutes. Extraction and drying were accomplished as previously described. The resultant wound dressing had a porosity of 28 microns on the skin contacting surface and a porosity of less than 0.2 microns on the external surface.

In the foregoing Examples of the preparation of wound dressings, if desired an adhesive may be applied to one surface for fixation to the wound site. A typical biocompatible adhesive may be formed in a solvent and spread to a thickness of between 0.001" and 0.01" onto a siliconized release paper. The solvent is then evaporated in the forced hot air oven leaving a solvent-free adhesive layer on the release paper. The wound dressing is then laminated with the adhesive layer, cut to size, packaged and sterilized.

Referring to FIG. 3, in the preparation of membranes to be used as wound dressings, the skin-contacting surface 44 is given a porosity which will permit absorption of liquid exudate from a wound and which optimally is in the range of 1 micron to 10 microns but may be increased to as much as 50 microns depending upon the amount of exudate to be removed from the wound. The opposite or external surface 48 is made porous to the extent of preventing bacterial penetration; i.e., less than 0.2 microns but preferably is porous only at a molecular level so as to permit transport of water vapor. The intermediate or intersticial thickness 46 between the opposite skin surfaces is characterized by being occupied by rather large voids which are separated laterally by less porous material. It has been found that these voids provide a degree of insulation to the wound which is of importance as the rate of healing is maximized when the wound is kept as close to normal body temperature as possible. Further, it has been observed that insulated wounds are less painful to the patient than those which are not insulated. Another important factor in controlling porosity of the wound dressing is to regulate the amount of moisture vapor transport which is the function both of the polymer type and porosity of the structure. Selective variation in the pore sizes of opposite surfaces of the wound dressing enables close control over the moisture vapor transport rate.

Different considerations enter into selection of porosity of opposing surfaces of a microporous membrane or vascular graft to be implanted into the body in determining the relative porosity of the surfaces. For example, if extensive fibrous ingrowth occurs, this is followed by contraction of fibrous tissue leading to constriction of capillaries, necrosis and/or calcification of the ingrown tissue. Such a condition may turn a compliant, flexible graft into a rigid tube subject to occlusive kinking and aneurism at the anastomosis and is more likely to occur in grafts having a porosity of 45 microns or greater. Thus, in accordance with the present invention, selective control of the pore size to less than 45 microns will afford the necessary control over ingrowth to yield a viable fibrohystiocytic tissue and capillaries. Shallow ingrowth sufficient to achieve adhesion between tissue and prosthesis but not leading to necrosis and calcification may be achieved with porosities from about 3 microns to 20 microns. When desired to prevent any ingrowth while permitting free transport of ions and soluble organic species may be achieved by forming the skin surfaces with porosities of less than 1 micron. Vascular grafts having outer surfaces with porosities in the range of less than 1 micron have demonstrated a similar freedom in tissue to the natural artery.

It is therefore to be understood that various modifications and changes may be made in the methods and resultant articles of manufacture of the present invention without departing from the spirit and scope thereof as defined by the appended claims.

We claim:

1. A microporous membrane comprising a unitary, biocompatible polyether-urethane sheet having a void volume in the range of about 50 percent to about 80 percent and layers of different pore sizes across the thickness dimension of the sheet; said sheet having porous surface skin layers on both sides thereof with a pore size in the range of about 0.1 micron to about 100 microns, and an intermediate layer defining relatively larger interstitial voids having a finger-like configuration and the longitudinal axes of the finger-like voids extending substantially normal to the surface skin layers.

2. The microporous membrane in accordance with claim 2 wherein opposite skin layers have different porosity.

3. The microporous membrane in accordance with claim 1 wherein a surface layer has a pore size in the range of about 0.1 microns to about 1 micron and contiguous thereto is a layer defining finger-like voids of about 100 microns by 200 microns.

4. The microporous membrane in accordance with claim 1 wherein a surface layer has a pore size in the range of about 2 microns to about 15 microns and contiguous thereto is a layer defining finger-like voids of about 200 microns by 500 microns.

5. The microporous membrane in accordance with claim 1 wherein one of the surface layers has a pore size in the range of about 1 micron to about 3 microns and the other of the surface layers has a pore size of less than about 0.2 microns.

6. The microporous membrane in accordance with claim 1 wherein one of the surface layers has a pore size in the range of about 3 microns to about 7 microns and the other of the surface layers has a pore size of less than about 0.2 microns.

7. The microporous membrane in accordance with claim 1 wherein one of the surface layers has a pore size of about 28 microns and the other of the surface layers has a pore size of less than about 0.2 microns.

* * * * *

UNITED STATES PATENT AND TRADEMARK OFFICE
CERTIFICATE OF CORRECTION

PATENT NO. : 4,813,966

DATED : March 21, 1989

INVENTOR(S) : D. Keith Gilding et al.

It is certified that error appears in the above-identified patent and that said Letters Patent is hereby corrected as shown below:

Col. 2, line 48, "socalled" should be -- so-called --.

Col. 12, line 42, "claim 2" should be -- claim 1 --.

Signed and Sealed this

Twelfth Day of December, 1989

*Attest:*

JEFFREY M. SAMUELS

*Attesting Officer*     *Acting Commissioner of Patents and Trademarks*